United States Patent
Hunter et al.

(10) Patent No.: US 10,253,615 B2
(45) Date of Patent: Apr. 9, 2019

(54) METHOD AND A SYSTEM FOR ULTRASONIC INSPECTION OF WELL BORES

(71) Applicant: NEDERLANDSE ORGANISATIE VOOR TOEGEPAST-NATUURWETENSCHAPPELIJK ONDERZOEK TNO, 's-Gravenhage (NL)

(72) Inventors: Alan Joseph Hunter, 's-Gravenhage (NL); Mariana De Soares Silva e Melo Mota, 's-Gravenhage (NL); Arno Willem Frederik Volker, 's-Gravenhage (NL)

(73) Assignee: NEDERLANDSE ORGANISATIE VOOR TOEGEPAST-NATUURWETENSCHAPPELIJK ONDERZOEK TNO, S-Gravenhage (NL)

( * ) Notice: Subject to any disclaimer, the term of this patent is extended or adjusted under 35 U.S.C. 154(b) by 302 days.

(21) Appl. No.: 15/120,017

(22) PCT Filed: Feb. 18, 2015

(86) PCT No.: PCT/NL2015/050101
§ 371 (c)(1),
(2) Date: Aug. 18, 2016

(87) PCT Pub. No.: WO2015/126243
PCT Pub. Date: Aug. 27, 2015

(65) Prior Publication Data
US 2017/0058660 A1    Mar. 2, 2017

(30) Foreign Application Priority Data
Feb. 18, 2014 (EP) .................................. 14155552

(51) Int. Cl.
*E21B 33/14* (2006.01)
*E21B 47/00* (2012.01)
(Continued)

(52) U.S. Cl.
CPC ....... *E21B 47/0005* (2013.01); *G01N 29/043* (2013.01); *G01N 29/07* (2013.01);
(Continued)

(58) Field of Classification Search
CPC .... G01N 29/043; G01N 29/07; G01N 29/075; G01N 29/42; G01N 29/44; E21B 47/0005
See application file for complete search history.

(56) References Cited

U.S. PATENT DOCUMENTS 3,401,772 A  9/1968 Kokesh
3,732,947 A  5/1973 Moran et al.
(Continued)

FOREIGN PATENT DOCUMENTS

EP  0263028 B1  1/1992
EP  1464959 A1  10/2004
(Continued)

OTHER PUBLICATIONS

Cement Evaluation Workshop, CBL-VDL. Schlumberger presentation. Apr. 2010.
(Continued)

*Primary Examiner* — Paul M. West
(74) *Attorney, Agent, or Firm* — McDermott Will & Emery LLP

(57) ABSTRACT

A well bore is inspected to detect cement defects that can give rise to leakage. The well bore comprises an inner metal pipe. Outside the inner metal pipe its configuration may vary with distance from the top of the well bore in terms of concentric pipes outside the inner metal pipe and presence of cement between the pipes. A probe with is lowered through
(Continued)

the inner metal pipe. An ultrasound signal is transmitted from the probe into the inner metal pipe and responses to the transmitted signal are received at a series of ultrasound receivers at different axial positions. A selection of a spatial frequency of waves arriving along the axial direction at the ultrasound receivers and/or the apparent velocity of said waves is retrieved dependent on the configuration. The received responses are band pass filtered accordingly. By selecting the band pass filter dependent on the configuration it becomes possible to detect cement defects well outside the innermost pipe from parameters of the earliest arriving pulse from the filtered reflection signal.

16 Claims, 10 Drawing Sheets

(51) Int. Cl.
*G01N 29/04* (2006.01)
*G01N 29/07* (2006.01)
*G01N 29/42* (2006.01)
*G01N 29/44* (2006.01)

(52) U.S. Cl.
CPC ............ *G01N 29/42* (2013.01); *G01N 29/44* (2013.01); *E21B 33/14* (2013.01); *G01N 2291/011* (2013.01); *G01N 2291/0232* (2013.01); *G01N 2291/0289* (2013.01); *G01N 2291/2636* (2013.01)

(56) References Cited

U.S. PATENT DOCUMENTS

| | | | |
|---|---|---|---|
| 3,747,702 A | | 7/1973 | Beil |
| 4,255,798 A | | 3/1981 | Havira |
| 4,382,290 A | | 5/1983 | Havira |
| 4,757,479 A | | 7/1988 | Masson et al. |
| 4,802,145 A | | 1/1989 | Mount, II |
| 4,834,209 A | * | 5/1989 | Vogel ...................... G01V 1/46 181/105 |
| 4,893,285 A | | 1/1990 | Masson et al. |
| 4,928,269 A | | 5/1990 | Kimball et al. |
| 4,951,266 A | | 8/1990 | Hsu |
| 4,992,994 A | | 2/1991 | Rambow et al. |
| 5,001,676 A | | 3/1991 | Broding |
| 5,089,989 A | | 2/1992 | Schmidt et al. |
| 5,640,371 A | | 6/1997 | Schmidt et al. |
| 7,663,969 B2 | | 2/2010 | Tang et al. |
| 7,885,142 B2 | | 2/2011 | Tello et al. |
| 2004/0122595 A1 | | 6/2004 | Valero |
| 2006/0285439 A1 | * | 12/2006 | Haugland ................ G01V 1/48 367/75 |
| 2007/0070810 A1 | | 3/2007 | Hurst et al. |
| 2007/0070816 A1 | | 3/2007 | Hurst et al. |
| 2009/0168597 A1 | | 7/2009 | Wu et al. |

FOREIGN PATENT DOCUMENTS

| | | |
|---|---|---|
| WO | 9935490 A1 | 7/1999 |
| WO | 03082366 A1 | 10/2003 |
| WO | 03083466 A2 | 10/2003 |

OTHER PUBLICATIONS

Cement Sheath Evaluation. API Technical Report 10 TR1. 2nd Edition, Sep. 2008.
Sinha, et al., "Influence of a Pipe Tool on Borehole Modes." Geophysics. May-Jun. 2009. vol. 74, pp. E111-E123.
Tubman, et al. "Synthetic Full Waveform Acoustic Logs in Cased Boreholes," Geophysics. Jul. 1984, vol. 49, pp. 1051-1059.
Simsek, et al., "An Efficient Formulation for Harmonic Waves in Multilayered Cylindrical Structures," IEEE—International Ultrasonics Symposium Proceedings. 2009. pp. 1483-1486.
Tubman, et al., "Synthetic Full-Waveform Acoustic Logs in Cased Boreholes, II—Poorly Bonded Casing," Geophysics. Apr. 1986, vol. 51. pp. 902-913.
Cheng, et al. "Elastic Wave Propagation in a Fluid-Filled Borehole and Synthetic Acoustic Logs," Geophysics. Jul. 1981, vol. 46, pp. 1042-1053.
Tang, et al. "Stoneley Wave Propagation in a Fluid-Filled Borehole with a Vertical Fracture," Geophysics. Apr. 1991, vol. 56, pp. 447-460.
International Search report and Written Opinion dated Jul. 16, 2015 in PCT Application No. PCT/NL2015/050101 (10 pages).
X.-M. Tang and A. Cheng, Quantitative Borehole Acoustic Methods, Handbook of Geophysical Exploration—Seismic Exploration, Elsevier, vol. 24, 2004, Chapters 2 and 3, pp. 31 to 109.

* cited by examiner

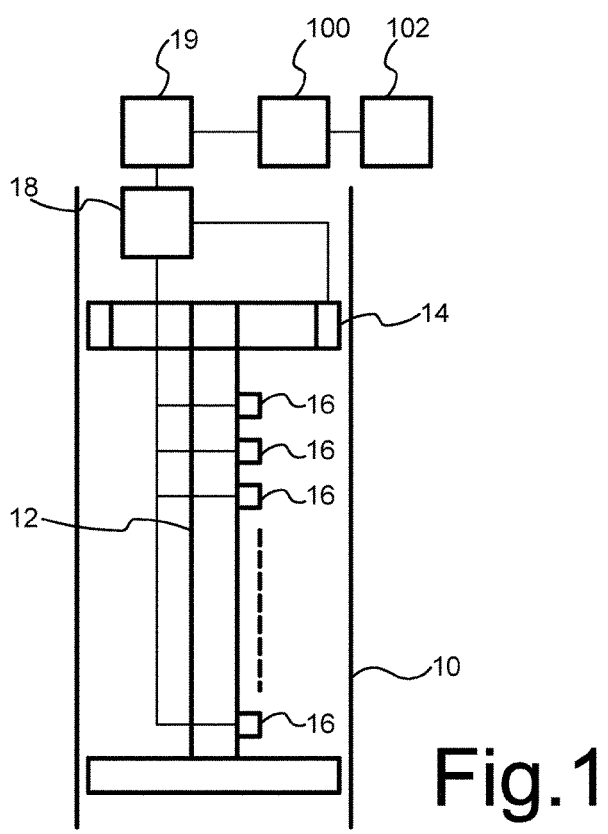

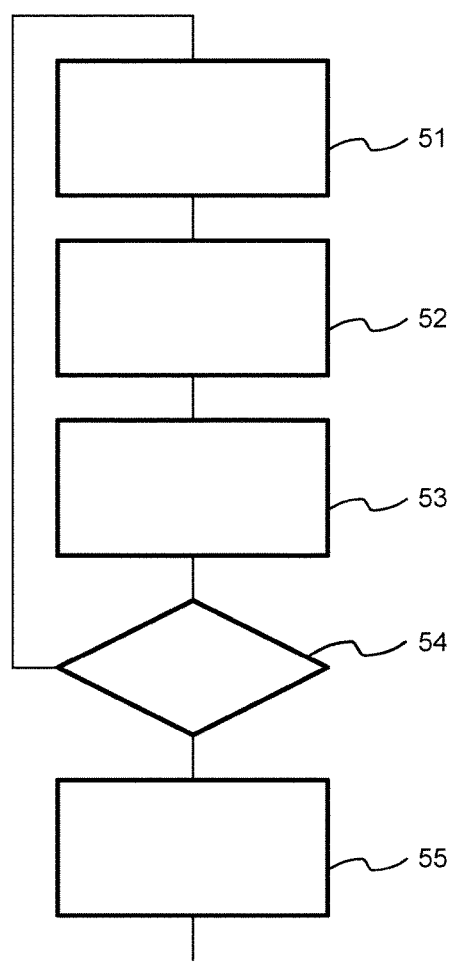

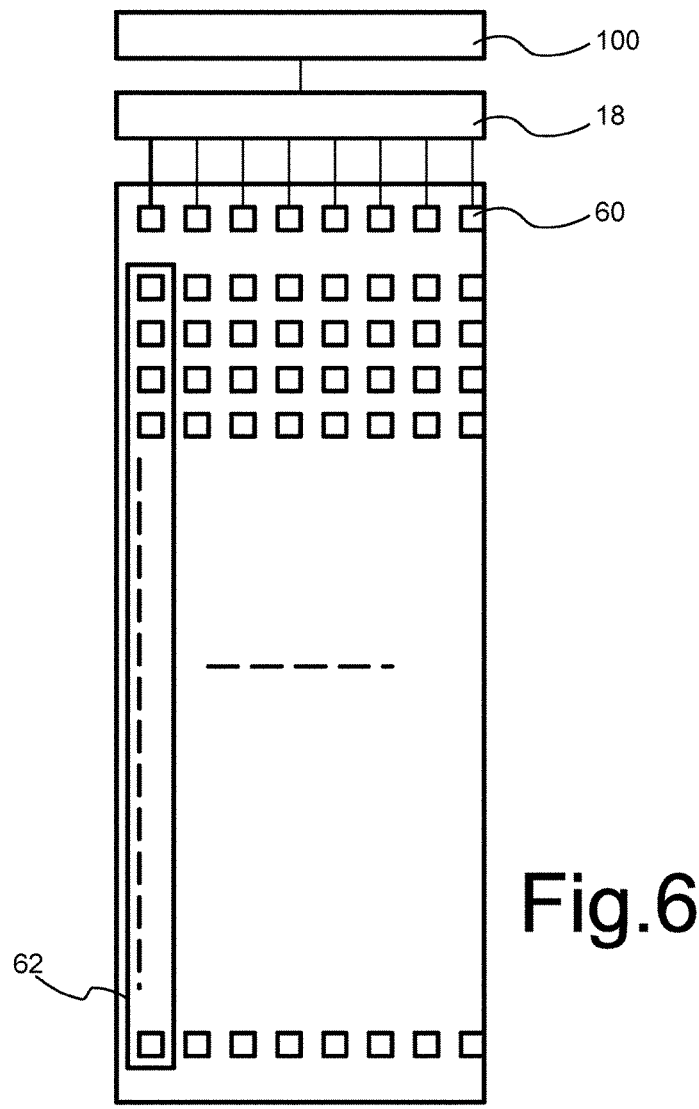

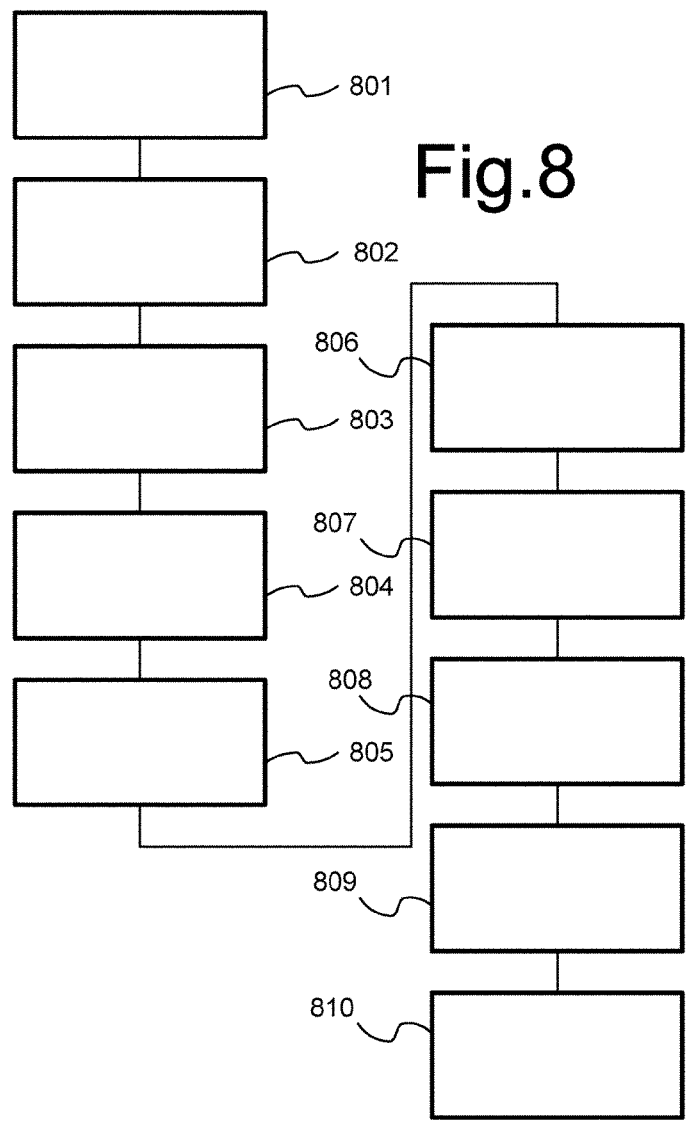

METHOD AND A SYSTEM FOR ULTRASONIC INSPECTION OF WELL BORES

CROSS REFERENCE TO RELATED APPLICATIONS

This application is a U.S. National Stage of International Application No. PCT/NL2015/050101, filed Feb. 18, 2015, which claims the benefit of and priority to European Patent Application No. 14155552.4, filed Feb. 18, 2014. The contents of both applications are hereby incorporated by reference in their entirety for all purposes.

FIELD OF THE INVENTION

The invention relates to a method and a system for ultrasonic inspection of well bores.

BACKGROUND

Oil wells typically comprise one or more concentric metal pipes in a bore hole through an earth formation. Usually, the diameter of the borehole decreases with distance from the top of the borehole and the number of concentric pipes decreases accordingly. Cement is provided between the outermost pipe and the earth formation outside the bore hole, and usually also between one or more pairs of radially successive pipes, although there may also be pairs of pipes without cement between them. The combination of one or more pipes and cement is referred to as a well bore.

The cement is used to prevent leakage through the well bore, for example from a deeper layer to the sea floor. Flaws in the cement can create a risk of leakage from the well bore. Two types of flaws can be distinguished: bond index loss and the presence of a micro annulus. The bond index is a measure of the fraction of space between successive pipes or between the outermost pipe and the surrounding formation that is filled by cement. Usually, if the bond index is less than a pre-determined threshold continuously over an interval of distance from the top of the well bore and the interval exceeds a predetermined length, this is considered to be an indication of a serious risk of leakage. A micro annulus is a lack of bonding of the cement to the pipe, which can also be a serious risk even if it does not present a dangerously low bond index.

It is known to use ultrasound pulse reflection measurements to test well bores for the presence of such flaws in the cement. A probe is lowered into the well bore through the inner pipe and ultrasound pulses are transmitted from the probe. The time of arrival and amplitude of the pulse is detected at a receiver. When measurements of the time of arrival or amplitude obtained show changes from a nominal measured time of arrival and amplitude when the probe is lowered, this is taken as an indication of the presence of flaws.

In practice, transmission of a pulse in a well bore does not result only in a single received pulse that is a copy of the transmitted pulse. The received pulse starts with a clearly distinguished delay after transmission, but it lasts much longer than the transmitted pulse. This is due to the availability of different transmission paths and wave modes in the well bore. The start of the reflected pulse can be associated uniquely with the fastest mode along the shortest path, but the later part of the received pulse is due to a mix of modes and paths. The signal components due to these modes and paths depend on the configuration of the well bore which are unrelated to flaws, and also on variations of intrinsic material properties or changes in the surrounding formation.

WO9935490 discloses ultrasonic inspection of a well bore. A transmitter and a receiver axially offset to the transmitter are used. A pulse is transmitted at an angle to the inner surface of the inner pipe of the well bore, so as to excite waves that travel axially through pipe. WO03083466, which refers to WO9935490, discloses use of a phased array of ultrasonic transducers to provide for transmission in a focused beam in the well bore without need for mechanical rotation. As disclosed in WO9935490, inhomogeneity in the cement, presence of fluid etc can give rise to wave scattering. WO9935490 relies on the fact that the cement-formation interface echoes depend on propagation through the cement. Their time delays depend on wave speed in the cement and cement thickness. Echo amplitudes depend on wave decay rate. If the echoes due to reflection from the cement formation interface can be identified, cement properties can be derived from the echoes and arrival time of echoes from scatterers can give information about the location of scatterers and the amplitude can give information about the size.

WO9935490 describes a wide variety of analysis techniques that can be used to extract information about the cement. The early arriving echo can be used to evaluate a pipe of the well bore for corrosion and perforations, or the presence of gas-like material at the first pipe-cement interface. Wave dispersion characteristics can be used to determine pipe thickness.

It is more difficult to obtain information from later arriving echoes that arrive after these early-arriving echoes, unless the later arriving echoes can be attributed to individual modes. WO9935490 describes processing of later arriving echoes to determine multiplicity for qualitative determination of cement strength, to determine propagation time inside the cement; and determination of whether echoes arose from scatterers in the cement or at the cement-formation interface. An inversion method is mentioned wherein the amplitude reduction of early-arriving echoes is used to estimate the beam profile that has been transmitted from the pipe into the cement, and later arriving echoes are used in conjunction with this beam profile to extract scattering information from the cement-formation echoes. However, this approach is useful only for later arriving echoes that can be distinguished.

It may be difficult to extract ultrasound information that is relevant for well bore inspection. Ultrasound inspection works best to provide complete results when the well bore contains only a single metal pipe between the inner space and the formation around the well bore. A well bore with a plurality of concentric pipes may have additional variability, such as changes in the number of concentric pipes, pipe diameters, pipe thickness, pipe material properties well bore diameter, cement properties, eccentricity of the pipes, well bore diameter, cement and fluid properties etc with distance from the top of the well bore, which give rise to ultrasound propagation changes that are unrelated to flaws in the cement. Moreover, it becomes difficult to interpret waves that may have penetrated beyond the first pipe-cement interface. Waves that leave the inner pipe outwardly are mainly reflected before they reach the interface between the cement and the surrounding rock formation, particularly at usual frequencies in the range above one hundred kilohertz. Better penetration can be achieved by using relatively low frequency ultrasound, with wavelengths larger than the distance between the pipes and the surrounding formation. But at these frequencies later arriving echoes are even more difficult to distinguish, and the well bore configuration still causes variations unrelated to flaws. The prior art provides only limited ways of extracting ultrasound information that is relevant for well bore inspection.

SUMMARY

Among others, it is an object to provide for selection of ultrasound inspection data that is useful for well bore inspection.

Among others, it is an object to provide a more robust well bore inspection method.

A method of monitoring cement defects in a well bore according to claim 1 is provided. Herein a probe is moved up and/or down the well bore. An ultrasound signal is emitted from the transmitter into the inner surface of the inner pipe of the well bore. Preferably an ultrasound transmitter pressed in contact with the surface of the inner pipe is used, to eliminate disturbance by contributions from reflections at the interface between fluid in the innermost pipe and the inner surface of that pipe. Responses to the transmitted signal are received by a series of ultrasound receivers in the well bore at successive axial distances from the transmitter. Band pass filtering is used that filters the received responses to pass selectively a part of the response corresponding to a predetermined apparent velocity component of wave travel along the axial direction at the ultrasound receivers and/or combination of temporal and spatial frequency corresponding to that apparent velocity component. It has been found that cement defects can be satisfactorily detected by band spatiotemporal pass filtering.

Dependent on the local configuration, a predetermined selection is made of the apparent velocity and/or a combination of a temporal frequency and the spatial frequency of the spatiotemporal pass band. Different selections are needed according to the number of concentric pipes in the configuration and optionally also according to other aspects of the configuration such as pipe diameter(s), pipe wall thickness, eccentricity of the pipes, pipe material type, indication of pairs of radially successive pipes between which cement has been injected, the type of cement used, overall well bore diameter and type of surrounding earth formation. For a given well bore, it is known in advance of inspection how these aspects vary with distance from the top of the well bore, so that the selection can be made dependent on this distance. The selection of the apparent velocity component in the axial direction may be retrieved from predetermined stored information dependent on this distance Detection of different types of defects may require band pass filtering at different spatial frequencies, apparent velocities and/or a combination of temporal frequency and spatial frequency. In an embodiment, band pass filtering the received responses is used to pass selectively respective parts of the response in a pass band at respective selected spatial frequencies, apparent velocities and/or combinations of temporal and spatial frequency. Herein a plurality of selected spatial frequencies, apparent velocities and/or combinations of temporal and spatial frequency may be used, i.e. at least one more than the selection mentioned in claim 1.

In an embodiment, the transmitted signal is a pulse signal. In this embodiment the band pass filtering preferably comprises computing a filtered time domain signal. The time of arrival, amplitude and/or wave phase of an earliest pulse in the filtered signal can be compared with a base line value to detect defects in the cement. It has been found that it is possible to detect cement defects in this way. Instead of using transmitted pulses other types of transmitted signals and their resulting reflections may be used, such as continuous signals with a swept frequency, from which pulse responses case can be synthesized in ways that are known per se. In this case, the band pass filtering may be realized by adapting the synthesis of pulse responses, for example by using weighing with selected frequency dependent phase and/or amplitude factors.

An inspection log may be generated indicating distances from the top of the wellbore and/or ranges of distances from the top of the wellbore where a difference between the time of arrival, amplitude and/or wave phase and a base line value exceeds a threshold value.

In an embodiment, the time of arrival, amplitude and/or phase determined at one or more other distances from the top of the wellbore to the transmitter are used to provide the base line value. An average of results from a range of other distances may be computed for example, or a value from a nearby distance may be used.

The band of temporal frequencies temporal frequencies is selected low compared to the frequencies at which ultrasound transmission in the well bore corresponds to travelling rays. Preferably, selected frequencies are used at which the ultrasound wavelength of bulk steel is larger than the pipe wall thickness, and preferably the ultrasound wavelength of bulk cement is larger than the distance between radially successive pipes. It has been found that this facilitates detection of cement defects beyond the innermost pipes, provided that band pass filtering is used.

In an embodiment, a predetermined band of temporal frequencies may be used, independent of the well bore configuration. It has been found that ultrasound frequencies in the range of 15-45 kHz are more indicative of cement flaws than other frequencies, probably because there is more ultrasound field strength in the cement due to wave mode effects (rather than ray effects) at these frequencies than at higher frequencies. In an embodiment, a predetermined temporal frequency band may be used that comprises at least temporal frequencies between 25 and 35 kHz and effectively no temporal frequencies above 50 kHz. Herein comprising effectively no temporal frequencies means wave energy above this frequency does not contribute significantly to the detection, e.g. that its transmitted energy is more than 10 db and preferably more than 20 db less than that of the energy at lower frequency.

In a further embodiment wherein a predetermined band of temporal frequencies may be used, independent of the well bore configuration, the band pass filtering of apparent velocities may comprise using a filtered signal that corresponds to a sum of the received responses within a predetermined temporal frequency band, delayed relative to each other by time delays corresponding to the apparent velocity selected for the distance from the top of the borehole to the transmitter. The sum may be computed explicitly or implicitly as part of Fourier transform computations for example.

A well bore inspection system is provided that is configured to execute the method. In an embodiment this system may comprise a circular array of transmitters including said transmitter in a plane perpendicular to the axial direction of the well bore. In this way circumferential angle dependent ultrasound patterns can be generated, to improve defect detection.

In an embodiment of the well bore inspection system the probe comprises a plurality of columns of successive ultrasound receivers. In this way circumferential angle dependent ultrasound reflection patterns can be detected, to improve defect detection.

In an embodiment of the well bore inspection system the probe comprises resilient elements configured to act between the supporting structure and a respective one of the ultrasound transmitters in the circular array, to push the ultrasound transmitter radially outward towards an inner surface of the inner pipe of the well bore. This may be used to eliminate contributions from fluid-inner pipe surface reflections at all transmitter positions.

BRIEF DESCRIPTION OF THE DRAWING

These and other objects and advantages will become apparent from a description of exemplary embodiments, with reference to the following figures.

FIG. 1 schematically shows a well bore inspection system
FIGS. 2a,b shows part of a well bore
FIG. 5 shows a flow-chart of operation of the processing system
FIG. 6 shows an embodiment of the probe comprising rings of transmitters and receivers

DETAILED DESCRIPTION OF EXEMPLARY EMBODIMENTS

Figure 2A:
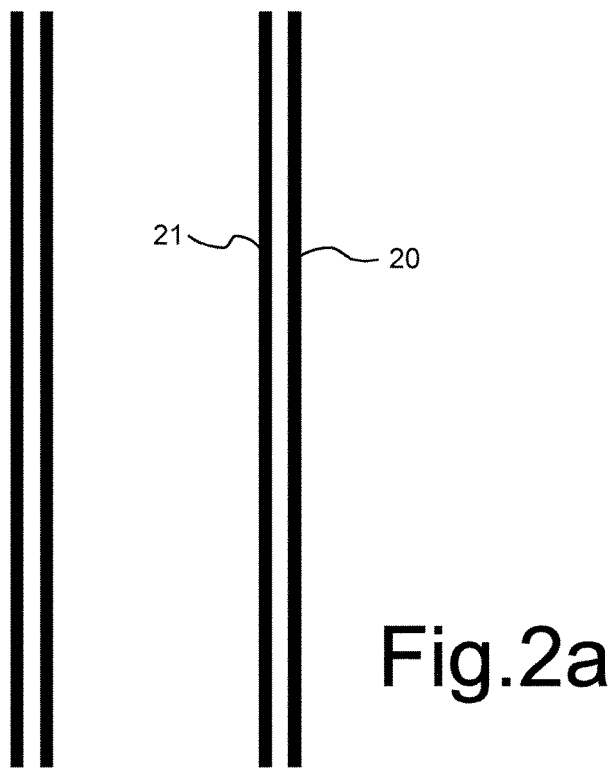

FIG. 1 schematically shows a well bore inspection system located within a pipe section 10 of a well bore. The system comprises a support structure 12, an ultrasound transmitter 14 on support structure 12, a series of ultrasound receivers 16, a control circuit 18 and a storage device 19. In addition a processing system 100 and a further storage device 102 for storing well bore configuration data are shown. A probe may be provided that comprises support structure 12, ultrasound transmitter 14, ultrasound receivers 16, control circuit 18 and storage device 19. Processing system 100 and a further storage device 102 need not be part of the probe: they may be coupled to the probe via a communication link, or they may be coupled temporarily at least to storage device 19, when the probe is taken outside the well.

Support structure 12 is an elongated structure, extending in the direction of the axis of pipe section 10. Ultrasound receivers 16 are mounted on support structure 12 at successive positions in the axial direction. In an embodiment, ultrasound receivers 16 are equally spaced. The illustrated number of receivers is selected only by way of example. In practice, many more receivers 16 at successively different axial positions may be used, for example at least a hundred, for example a hundred and twenty eight. Preferably, all ultrasound receivers 16 are mounted on the same axial side with respect to ultrasound transmitter 14. In another embodiment ultrasound receivers 16 may be mounted on both axial sides of ultrasound transmitter 14. When ultrasound receivers 16 on one side are used, a higher spatial resolution is possible with the same number of ultrasound receivers 16. Ultrasound receivers 16 on both sides make it possible to detect responses at apparent velocities with different signs. In an embodiment the distance between the ultrasound receivers 16 that are furthest apart is at least one meter, e.g. two meters.

Control circuit 18 and storage device 19 may be located in or on support structure 12. Control circuit 18 is coupled to ultrasound transmitter 14, ultrasound receivers 16 and storage device 19. Processing system 100 is shown coupled to storage device 19 a further storage device 102. As noted the coupling to storage device 19 may be realized temporarily, when the probe is outside the well, or via a communication link.

As is well known per se, a well bore may be constructed by drilling, lowering pipe sections and injecting cement in the space between the outer surface of the pipe sections and the surrounding earth formation, such as rock. In simple well bores, a single pipe section is used between the axis of the well bore and the surrounding formation, the interior of the pipe being used for material transport and space between the pipe and the formation being filled with cement. In more complicated well bores, a plurality of concentric pipes is used.

Figure 2B:
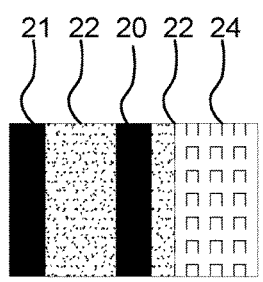

FIG. 2a shows part of a well bore, comprising inner pipe sections 21 surrounded by outer pipe sections 20. With increasing distance from the top of the well bore, the number of concentric pipes typically decreases. Thus a narrower pipe section becomes the outermost pipe section 20. FIG. 2b shows a detail of a well bore, with an inner pipe section 21, an outer pipe section 20, surrounding cement 22 and the surrounding formation 24. Cement may also be provided between the inner pipe 10 and the outer pipe 20. In another configuration, fluid may be provided between these pipes. Although the inner and outer pipe are ideally coaxial, in practice they may be locally eccentric. The inner pipe sections 10 may be filled with a fluid such as water. By way of example, the innermost pipe section may be of steel with diameter of between 7-12 inch (170-300 mm) for example and a pipe wall thickness of between 8-20 mm. The outer pipe 20 section may be of steel with a thickness in a similar range and a spacing between 20 and 100 mm from the inner pipe 10 may be used. Although two concentric pipes are shown, more may be used, for example up to five pipes with spacings between 20 and 100 mm. The outermost pipe may have diameter of between 7-18 inch (170-450 mm) and the well bore may be up to 500 mm wide.

In turn the outermost pipe may have a similar spacing to the surrounding formation. The speed of sound in bulk steel is about 3-6 kilometer per second, dependent on the type of wave. But the speed in pipewalls can be much slower if the wavelength is not much shorter than the wall thickness. The same holds for cement, which has a speed of sound in the order of 2-4 kilometer per second.

The purpose of well bore cement inspection is to ensure that no defects are present in the cement or the bonds between the cement and pipe that would allow fluid to escape to the surface, or to permeable strata below the surface, through the cement. Local cracks or voids may be tolerated, as long as they do not extend over more than a predetermined length in the axial direction.

In operation, support structure 12 is lowered into the inner pipe of the well bore, through successive pipe sections 10. At a number of heights in the well bore measurements are performed. This may be done while support structure 12 is lowered and/or raised. During a measurement, control circuit 18 of the well bore inspection system repeatedly causes ultrasound transmitter 14 to transmit an ultrasound pulse into the adjacent pipe section 10. Preferably, ultrasound transmitter 14 is kept in contact with the surface of the adjacent pipe section 10 during transmission. The ultrasound pulse may have length of between 10-100 microsecond for example, containing oscillations in a frequency range of 15-45 kHz for example. Optionally, the frequency range may be selected dependent on the distance to the top of the well bore, in correspondence with filter settings for the received signal, which will be described in the following.

Ultrasound receivers 16 receive responses to the pulse from the pipe section 10. Control circuit 18 causes the responses to be recorded in storage device 19, the recorded responses represent the response at each ultrasound receiver 16 as a function of time from transmission of the pulse.

In association with the recorded responses, control circuit 18 may record information to indicate the probe-borehole top distances at which the responses to different pulses were measured, e.g. the distance from the probe to the earth surface. In an embodiment, control circuit 18 records time stamps, and another part of the system (e.g. at the earth surface, not shown) may record probe-borehole top distance as a function of time, e.g. based on cable length to the probe. However, any other means of recording information indicative of probe-borehole top distance may be used.

Each pulse excites a plurality of transmission modes in the pipe, which may have mutually different propagation speed. For the inspection of cement, use is made of modes that travel along the axial length of the pipes. The received response is the result of a plurality of transmission modes.

Figure 3:
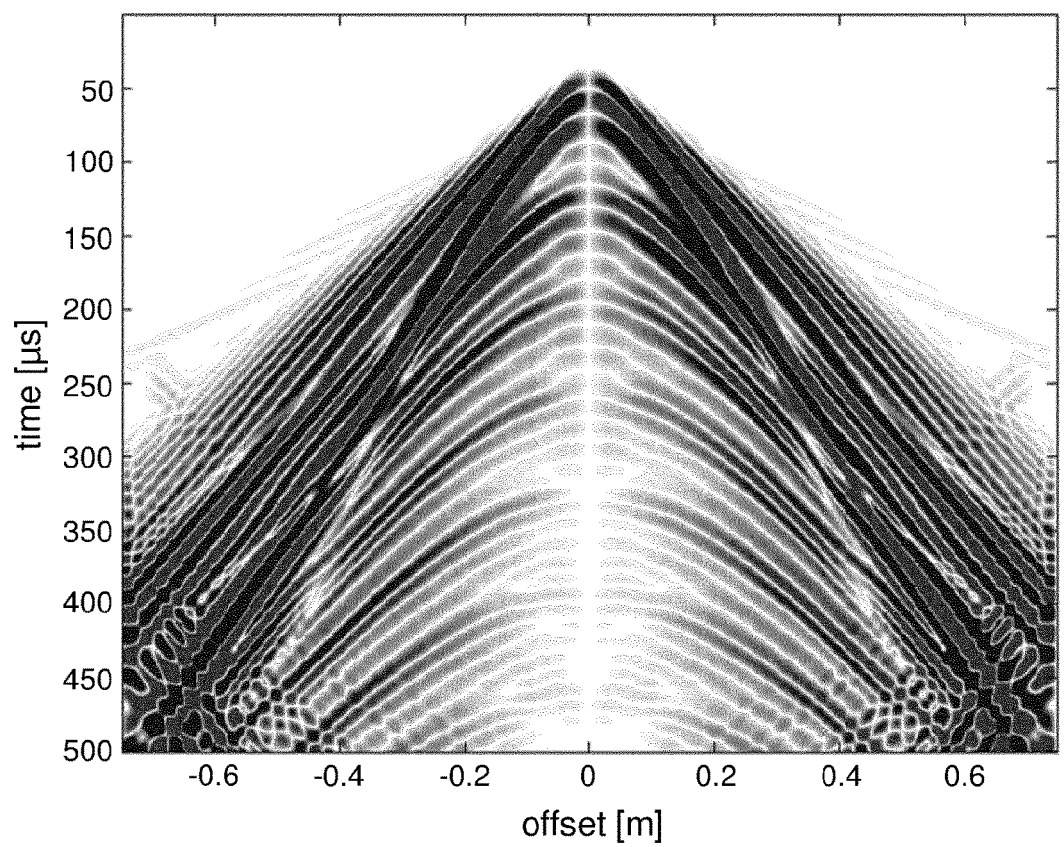
FIG. 3 shows a plot of receiver position (horizontally) and time delay from transmission (vertically downward)

FIG. 3 shows a simulation plot of receiver position (horizontally) and time delay from transmission (vertically downward) at which large signal amplitudes $R(x, t)$ are received in response to a transmitted pulse for a simulated well bore. The first received signals correspond to the excited mode with the largest ultrasound propagation speed. This time delay of the first received signals increases with distance of the receiver from the transmitter. Furthermore, arrival times of some slower modes with greater time delays can be distinguished. However, in most cases the signals due to different modes are mixed up, so that clear arrival times cannot be distinguished for all modes.

Wave components in the modes that travel along the pipes also have some amplitude in the cement adjacent the pipe. This amplitude generally decreases with distance from the pipes in the cement. The half value distance, that is, the distance from the pipes at which the amplitude in the cement decreases to half its value immediately next to the pipe, decreases with the spatial frequency of the wave, and hence also with its temporal frequency. When relatively low temporal frequencies are used, e.g. in the 15-45 kHz range, at which the wavelength in bulk steel is already 60-600 millimeter, i.e. larger than the pipewall thickness, the half value distance is relatively large, for example not much smaller than the distance to the cement-formation interface.

This means that the wave propagation speed and/or attenuation at such low frequencies are mainly affected by properties of the cement-pipe boundary conditions, such as bond index or the presence of a micro annulus, as well as by properties of the cement. This effect is used to inspect the well bore. The time of arrival, amplitude and/or phase of the received pulse may be used as a measure of cement properties. In the unprocessed signals this is only possible for the earliest arriving part of the pulse. However, when the well bore contains multiple concentric pipes this part of the pulse is mainly due to wave propagation in the innermost pipe, or at least the variation of the time of arrival, amplitude and/or phase depends mostly on variations of the spatial relation between the pipes and not on flaws in the cement.

From simulations, the inventors have discovered that the time of arrival, amplitude and/or phase of arriving pulses of the first reflection of only a few components the reflected signal provide useful information about flaws of the cement.

FIGS. 4a-d illustrates simulated ultrasound reflections from a well bore with a configuration containing three pipes and two layers of cement between the pipes, with pulses containing ultrasound frequencies in a band of 15-30 kHz. Ultrasound signals as a function of time are shown, obtained from a combination of receivers after filtering to pass selected apparent velocities in the inner pipe. These, apparent velocities correspond to different angles of resulting wave fronts radiated towards the receivers inside that inner pipe.

Figure 4A:
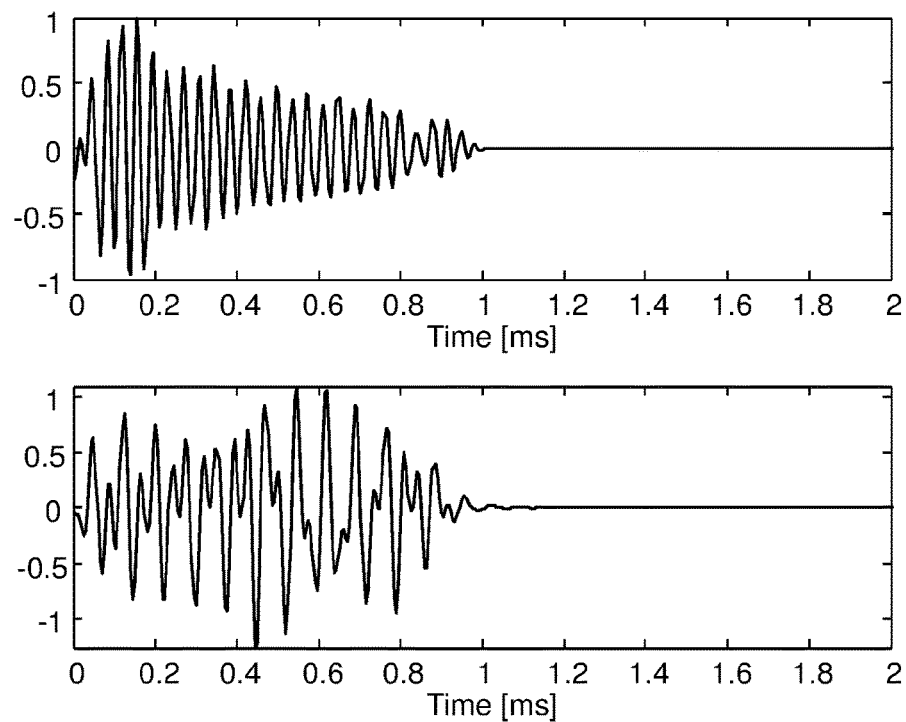
FIGS. 4a-e illustrate of sensitivity to flaws under various circumstances

FIG. 4a shows signals from well bores with and without cement at zero angle, that is, of a plain sum of the signals from the different receivers. As can be seen, the flaws have a complex effect on the content of the signal.

Figure 4B:
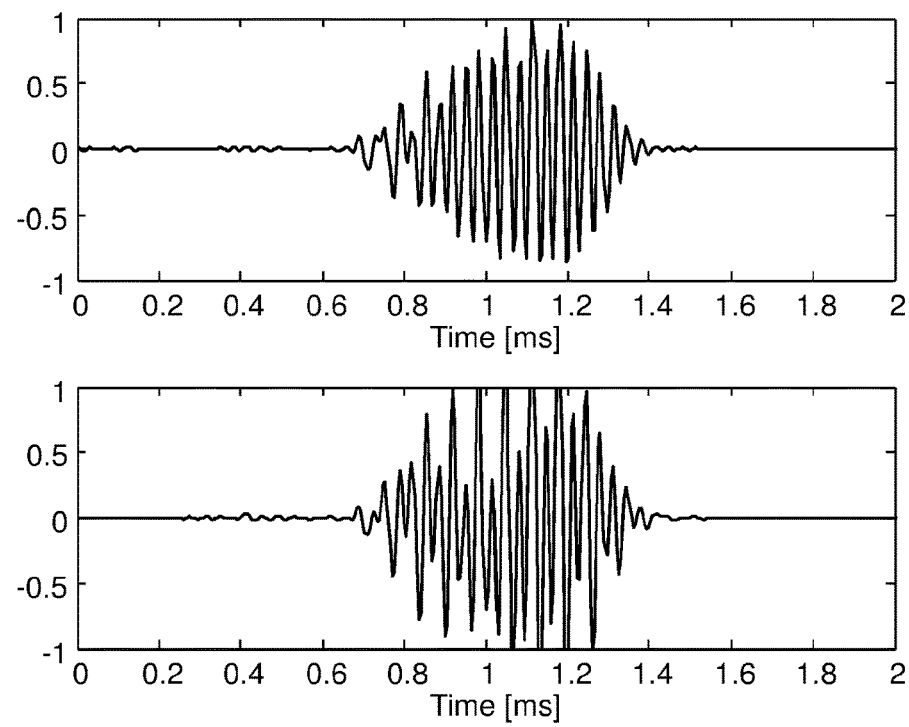

FIG. 4b shows signals at an angle of thirty degrees, that is, of a sum of the signals from the different receivers multiplied by phase factors that compensate for relative travel distance difference of a wave front at this angle to different receivers. As can be seen, the flaws again have a complex effect on the content of the signal.

Figure 4C:
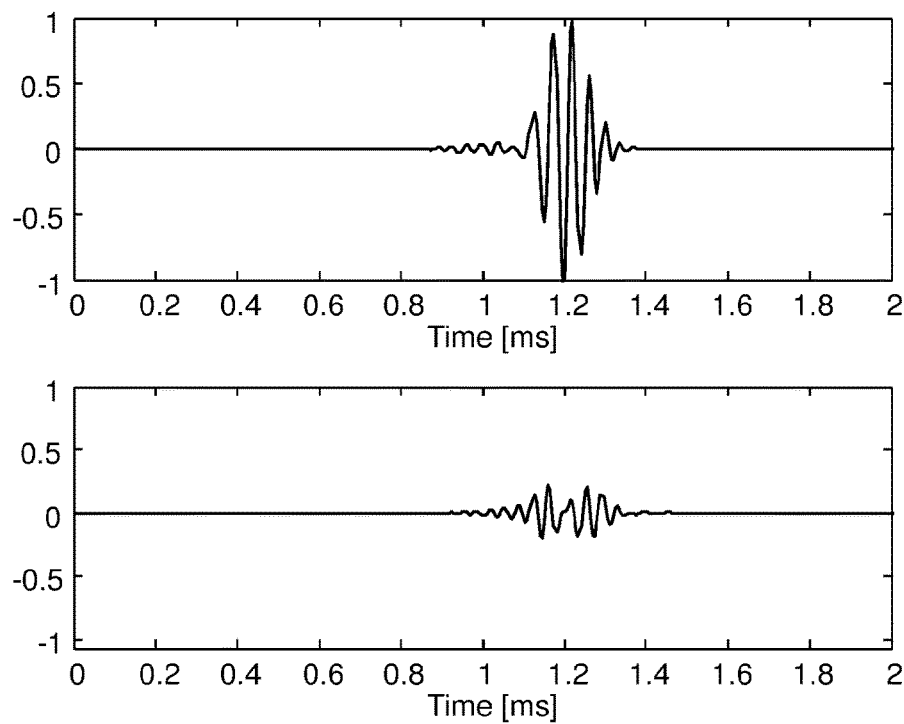
Figure 4D:
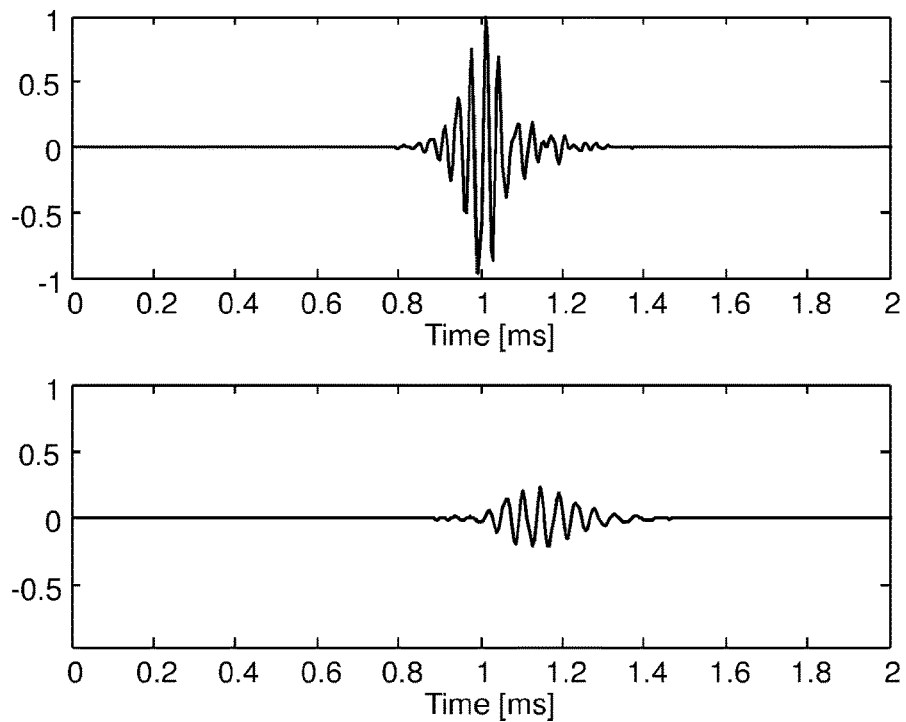

FIG. 4c shows signals at an angle of sixty degrees. As can be seen at this angle the effect of flaws translates directly into an change of amplitude of the signal. FIG. 4d shows signals at an angle of 49.8 degrees, which was found to be optimal for detection. At this angle the effect of flaws also translates directly into an change of amplitude and time of arrival of the signal.

Figure 4E:
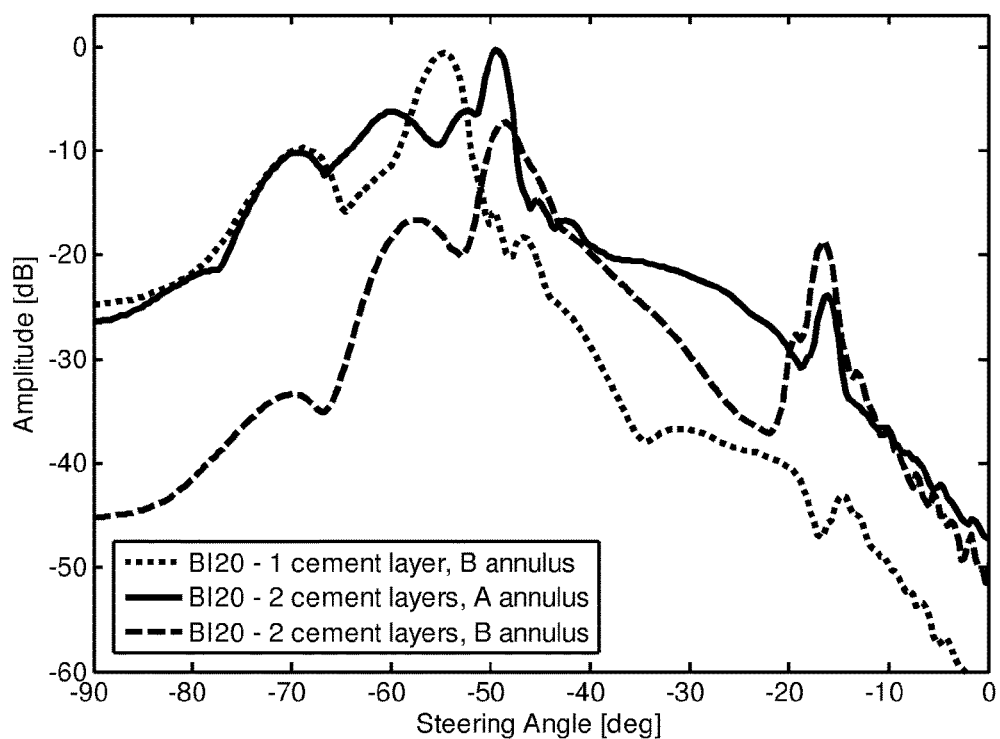

FIG. 4e shows the ratio between the difference of the amplitudes in the presence and absence of flaws, relative to the signal without flaws in decibels as a function of the angle for different configurations for pulses with ultrasound frequencies in the range of 15 kHz-30 kHz. The solid line corresponds to a 20% bond index defect in the A-annulus in a well bore configuration with two cement layers. The dashed line corresponds to a 20% bond index defect in the B-annulus in the bore configuration with two cement layers. The dotted line corresponds to a 20% bond index defect in a configuration with cement in the B-annulus and water in the A-annulus. The angles that are most sensitive to bond index defects correspond to the highest peaks.

Moreover, it has been found that the selection of parts of the signal that best show the flaws depends on the overall well bore configuration, so that different selections are needed for different well bores, and may even be needed at different distances from the top of the well bore within the same well bore. The selection of parts of the signal that will best show flaws varies with well bore configuration to such an extent that no single form of additional processing could be identified that has optimal sensitivity to relevant flaws in the cement everywhere within the same well bore with multiple concentric pipes.

In an embodiment, processing system 100 operates to extract information about the cement integrity from the recorded responses by spatio-temporal filtering of the received signals, followed by detection of the first arriving pulse in the filtered signal and measurement of its time of arrival, amplitude and/or phase. In an embodiment, this processing may be done while the probe is in the well bore, after transmission of the recorded responses to processing system 100. In another embodiment, processing may be done after the probe has been removed from the well bore, when storage device 19 has been coupled to processing system 100.

FIG. 5 shows a flow-chart of operation of processing system 100. In a first step 51, processing system 100 selects a set of received responses to a pulse and retrieves information from further storage device 19 that indicates the spatial frequency, or combination of spatial and temporal frequencies (or frequency band) that should be used for this set. Alternatively, the selection may be indicated by a selected apparent velocity value along the array of receivers. The information is selected dependent on the probe-to-top-of-borehole distance at which the set of received responses to the pulse was obtained.

Control circuit 18 may record information indicating the probe-borehole-top distances associated with different recorded responses, in addition to sample values of the received signals at a set of time points and axial distances relative to the time of transmission of a pulse and the axial location of the transmitter. Optionally parameters of the transmission, such as its amplitude, may recorded if the same parameters are not used each time.

Processing system 100 may be configured to use the information indicating a probe-borehole-top distance to retrieve the spatial frequency, spatiotemporal frequency combination and/or apparent velocity dependent on the probe-borehole top distance. The information that indicates the spatial frequency and/or combination may be an explicit indication of a central spatial frequency "k" and/or a spatial frequency "k" plus temporal frequency "f" combination, or an apparent velocity value to be used for defining the filtering that should be applies to the signals obtained at a probe-borehole top distance. In an embodiment, the information that indicates the spatial frequency k for use in combination with a predetermined temporal frequency range that is the same for all probe-borehole-top distances.

The information that indicates the spatial frequency and/or the combination may be an explicit indication of the spatial frequency k, apparent velocity and/or (k, f) combination dependent on the probe-top of borehole distance, or an indication of the well bore configuration dependent on this distance, a table relating well bore configurations to spatial frequency k, apparent velocity and/or (k, f) combination being used to translate the indication of the well bore configuration. The dependence on probe-borehole top distance may be represented for example as information defining distance ranges and for each range information that indicates spatial frequency k, apparent velocity and/or (k, f) combination, or a table with entries for different distances, each entry containing information that indicates the spatial frequency, apparent velocity and/or combination of spatial and temporal frequencies.

In a second step 52, processing system 100 receives data representing the selected set of received responses R(x,t) at receivers 16 at different axial distances "x" from transmitter 14, at a series of different time delays "t" from transmission of the pulse by transmitter 14, for a given probe-borehole top distance. Although second step 52 is described for an off-line embodiment, using recorded responses sampled at predetermined time points relative to the transmission, it may be noted that alternatively a real-time embodiment may be used, wherein second step 52 comprises causing ultrasound transmitter 14 to transmit an ultrasound pulse into the adjacent pipe section 10.

In a real-time embodiment, second step 52 may comprise causing ultrasound transmitter 14 to transmit an ultrasound pulse into the adjacent pipe section 10 and capturing samples of response signal values R(x,t). In a third step 53, processing system 100 filters the received responses R(x,t) using a bandpass filter with a passband at defined by the indicated spatial frequency k and/or (k, f) combination that is adaptively defined by the spatial frequency k and/or (k, f) combination from first step 51 (as used herein "bandpass filter(ing)" also covers a filter that passes a single frequency k or frequency combination (k, f) only. In an embodiment, filtering comprises computing the Fourier transform $S(k,f)$ of $R(x,t)$ as a function of spatial frequency k and temporal frequency f and extracting information from the Fourier transform values $S(k,f)$ in a frequency band defined by k or (k, f) that processing system 100 has selected dependent on the information from further storage device 19. An inverse Fourier transform of the extracted information with respect to time may then be used to obtain a filtered time response $R'(t)$. the time of arrival, amplitude and/or phase of the first peak of $R'(t)$ can be used to detect defects.

In the embodiment wherein a predetermined temporal frequency range is used, processing system 100 may perform the filtering of third step 53 by using a pass band filter that passes ultrasound with apparent velocity in a velocity band around the apparent velocity selected for probe-borehole top distance. The filtered signal may be computed in any one of a number of ways. In an embodiment processing system 100 may perform the filtering based on apparent velocity by computing the Fourier transform $S(k,f)$ with $k=f/c'$ where $c'$ is the selected apparent velocity. The apparent velocity can be associated with an angle of a selected wave front $c'=c*\sin(\text{angle})$. At least for configurations with two concentric pipes and no more, the angle of a selected wave front is preferably in a range of forty five to sixty five degrees. It has been found that first reflections obtain with filtering corresponding to these angles allows for detection of flaws. The inverse Fourier transform of $S(f/c', f)$ with respect to temporal frequency yields a filtered time response function $R'(t)$ of which the time of arrival, amplitude and/or phase of the first peak can be used to detect defects. Instead of $S(k,f)$ with $k=f/c'$ a sum of $S(k, f)$ values with k values in a band of spatial frequencies around $k=f/c'$ may be used in this computation of $R'(t)$. Alternatively, processing system 100 may perform a corresponding time domain filter computation to compute $R'(t)$.

From a fourth step 54, processing system 100 proceeds to a fifth step 55 if received responses R(x,t) for a predetermined range of probe-borehole top distances (e.g. the entire well bore) have been processed. Otherwise, processing system 100 repeats from first step 51 for a next probe-borehole top distance.

In a fifth step 55, processing system 100 detects a first arriving pulse in the filtered signals $R'(t)$ for different probe-borehole top distances, and determines the time of arrival, amplitude and/or phase of that pulse relative to the transmitted pulse. For this purpose, time of transmission, amplitude and/or phase of the transmitted pulse may be determined from the timing and/or parameter used by control circuit 18 to cause ultrasound transmitter 14 to transmit an ultrasound pulse into the adjacent pipe section 10.

From the time of arrival, amplitude and/or phase, processing system 100 generates inspection information by comparing the time of arrival, amplitude and/or phase determined from the adaptively filtered responses at the different probe-borehole top distances with baseline time of arrival, amplitude and/or phase values. In an embodiment, for each distance the time of arrival, amplitude and/or phase determined for an adjacent distance is used as baseline. In an another embodiment, baseline values may be determined from a plurality of values measured for different probe-top of borehole distances, for example as an average, a median, or by low pass filtering. In another embodiment, recorded time of arrival, amplitude and/or phase for the same probe-top of borehole distance measured during an earlier inspection may be used.

Comparing may comprise detecting probe-borehole top distances at which the time of arrival, amplitude and/or phase differ by more than a threshold from the baseline. An inspection log may be generated that indicates the probe-borehole top distances for which differences in excess of the threshold have been detected, for example in the form of an image wherein these probe-borehole top distances have been marked. The information retrieved from further storage device 19 in first step 51 may additionally comprise information indicating which one or which combination of differences between baseline and measured time of arrival, amplitude and phase should be used at a given probe-top of borehole distance.

A combination of measurements of multiple ones of time of arrival, amplitude and phase may be used to increase robustness of detection of the same type of defect, for example by detecting a defect if a change in excess of a threshold has been detected at least from a predetermined number of time of arrival, amplitude and/or phase measurements. The predetermined number may be one, resulting in an OR requirement (or the time of arrival differs by more than a threshold from the baseline, or the amplitude differs by more than a threshold from the baseline, or the phase differs by more than a threshold from the baseline) that reduces false negative detections, or equal to the number of selected combinations, resulting in an AND requirement that reduces false positive detections.

Although an embodiment has been described wherein spatial and temporal filtering are performed for a single spatial frequency (band), a single apparent velocity (band) or a single combination (band) of spatial and temporal frequencies or area of such combinations, it should be appreciated that instead a plurality of filter operations for respective ones of a plurality of combinations of spatial and temporal frequencies or areas of such combinations may be used. Different combinations may be used to monitor different types of flaw in the cement. For example, one set of combinations may be used to detect bond index defects, and a different combination may be used to detect micro annuli. Also, similar to use of more than one of time of arrival, amplitude and/or phase, multiple selected combinations may be used to increase robustness of detection of the same type of defect.

Although an embodiment has been described wherein spatial and temporal filtering are performed together, using received responses to a transmitted ultrasound pulse that contains a band of ultrasound frequencies, it should be appreciated that instead narrow band pulses at the selected temporal frequencies may be transmitted, in which no temporal filtering may be needed. In an embodiment, control circuit 18 is configured to obtain information indicating the temporal frequencies to be used in the transmitted pulses, and to control ultrasound transmitter 14 to transmit band limited pulses, limited to the selected temporal frequency bands. Control circuit 18 may be configured to obtain information indicating the probe-top of borehole distance, for example via a communication link (not shown in FIG. 1) from the top of the borehole to control circuit 18, or using a sensor, e.g. a pressure sensor or a pipe segment weld detection sensor and weld counter (not shown). Control circuit 18 may be provided with data that relates the information indicating the probe-top of borehole distance to selected frequency dependent on distance.

When ultrasound transmitter 14 is controlled to transmit pulses at selected frequencies dependent on probe-top of borehole distance, processing system 100 does not need to perform temporal filtering, or a modified filter may be used to perform temporal filtering.

Although an embodiment has been described wherein the filtering in third step 53 involves the computation of the Fourier transform, it should be appreciated that instead the computation of the Fourier transform for all f, k values may be omitted. In an embodiment, only the Fourier transform for a band of k values around the selected k value, or f, k combination is computed from the responses R(x,t). In another embodiment, a sum of products of the responses R(x,t) with coefficients C(x,t) is computed, wherein first step 51 comprises selecting a set of coefficients C(x,t) dependent on probe-borehole top distance, the set being selected so that the spectral components of R(x,t) at the selected f, k combination are emphasized relative to other components of R(x,t).

Although an embodiment has been described wherein processing system 100 generates inspection information by comparing the difference with baseline data to a threshold, other ways of generating inspection information may be used, for example by including differences between the measured values and the baseline data for successive probe-borehole top distances in an inspection log.

In a preferred embodiment, the pulses are excited by an ultrasound transmitter on the probe that is in mechanical contact with the innermost pipe, so that there is a form of ultrasound transmission from the transmitter to the pipe that does not pass through the fluid. This helps to suppress contributions to the received pulses from waves that have traveled through the fluid, making it easier to isolate modes of which the time of arrival, amplitude and/or phase depends detectably on flaws in the cement. It has been found that under some circumstances contributions from waves that have traveled through the fluid can make it impossible to find detectable pulses of this type.

FIG. 6 shows an embodiment of the probe comprising a ring of transmitters 60 and a plurality of columns 62 of receivers mounted at successive circumferential positions along the probe. Herein, a circumferential array of ultrasound transmitters and a circumferential array of axial columns of receivers are used as a phased array. This makes it possible to generate different beam patterns, with main transmission lobes in successively different radial directions and/or beams with different spatial frequency along the array. This makes it possible to perform detection dependent on circumferential wave direction and/or circumferential spatial frequency. It has been found that this makes it easier to isolate modes of which the time of arrival, amplitude and/or phase depends detectably on flaws in the cement. Moreover, it may make it possible to distinguish flaws that occur consistently in the same circumferential direction at successive probe-top of borehole distances from flaws that occur in different directions, which may not give rise to a risk of leakage.

Control circuit 18 may be configured to cause transmitters 60 to transmit ultrasound pulses one after the other, or successively with different phase relations between the oscillations in ultrasound pulses from different transmitters 60, e.g. corresponding to different circumferential frequencies, or to shape beams in respective circumferential directions. Control circuit 18 may be configured to record receive ultrasound responses to each of these successive pulses respectively. Processing system 100 may be configured to apply band pass filtering of circumferential frequencies in the received responses, or to shape circumferential direction dependent reception patterns. The resulting data may be processed as described for the single transmitter embodiment.

Figure 7:
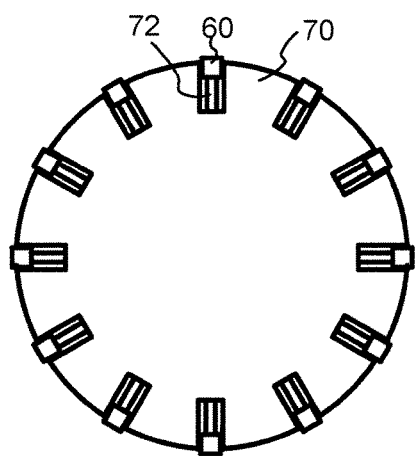
FIG. 7 shows a top view of a ring of ultrasound transmitters
FIG. 8 a flow chart of spatiotemporal frequency selection

FIG. 7 shows a top view of a ring of ultrasound transmitters 60 in a probe. The probe contains a supporting structure 70 and resilient elements 72 such as springs. Each resilient element 72 is configured to act between supporting structure 70 and a respective one of the ultrasound transmitters 60, to push the ultrasound transmitter 60 radially outward towards the inner surface of the inner pipe, to bring the ultrasound transmitter 60 into contact with the inner surface. Supporting structure 70 may comprise radially extending holes along its circumference, ultrasound transmitter 60 being located radially movable in the holes, the resilient element 72 being located in the holes between the supporting structure 70 and the ultrasound transmitter 60. Instead of holes, slots in the supporting structure 70, cylinders that protrude from supporting structure 70 etc may be used as guide structures to direct movement of ultrasound transmitter 60 in the radial direction.

Preferably, simulation is used to select the combinations of spatial and temporal frequencies that should be used to detect flaws. Simulation makes it possible to evaluate how much the time of arrival, amplitude and/or phase change at different combinations of spatial and temporal frequencies, due a range of variations in the well bore configuration that do not correspond to flaws, such as variation of the number of concentric pipes in the well bore configuration, pipe diameter(s), pipe wall thickness, eccentricity of the pipes, pipe material type, an indication of pairs of radially successive pipes between which cement has been injected, the type of cement used, overall well bore diameter and type of surrounding earth formation. Similarly, simulation makes it possible to evaluate the how much the time of arrival, amplitude and/or phase change at different combinations of spatial and temporal frequencies, due a range of flaws, such as various flaws that affect the bond index. The availability of evaluations over a range of variations facilitates selection of useful combinations of spatial and temporal frequencies, and/or useful ones of the time of arrival, amplitude and phase.

For the simulation, finite difference or finite element elastic models of well bore configurations may be used for example. Finite element elastic models are known per se, e.g. using Hooke's law, and provide for modeling of different elastic properties in the steel pipes, the cement and the fluid in the well bore.

FIG. 8 shows a flow chart of computer implemented spatiotemporal frequency selection using a simulation process. In a first step 801 a baseline configuration is provided. In one example, the baseline configuration defines the existence of two concentric steel pipes, with specified pipe diameters and pipe wall thickness and a distance to the surrounding formation and water in the inner pipe, with cement between the outer pipe and the formation and water and/or cement between the pipes.

In a second step 802, the ultrasound vibration field in response to ultrasound excitation is simulated according to the base line model. In a third step 803, variations of the model are generated by introducing flaws. For example, for bond index flaws variations may be introduced that include a model with missing cement over a single circumferential section, a model with two such sections, a model with three such sections, a model with wherein the outer pipe is eccentric with respect to the hole in the surrounding formation and wherein no cement is present in a circumferential sector that includes the circumferential angle at which the outer pipe is closest to the surrounding formation etc. In a fourth step 804, the ultrasound vibration fields in response to ultrasound excitation is simulated according to each of these models are computed.

In a fifth step 805, innocent variations of the model that do not include flaws are selected. For example, the variations may be selected that include models with various eccentricities of the pipes with flawless cement, corrosion of the pipe surface, different sizes of the hole in the surrounding formation, surrounding formations with different acoustic properties etc.

In a sixth step 806, filtered versions of the responses are computed, obtained by spatiotemporal band pass filters with centre frequencies on respective locations on a grid of possible combinations of spatial and temporal frequencies for the responses obtained from baseline model and the variations. In a seventh step 807, the time of arrival, amplitude and phase of received pulses in the filtered signals according to the models are computed.

In an eight step 808, the results are mapped onto a spatial and temporal frequency space, adding first markings at spatial and temporal frequencies where the innocent variations of the model result in changes from the baseline time of arrival, amplitude and/or phase of the filtered signal that exceed a first predetermined threshold. Furthermore, second markings are applied to spatial and temporal frequencies where at least one flaw containing variation of the model results in changes from the baseline time of arrival, amplitude and/or phase of the filtered signal that exceed a second predetermined threshold.

In a ninth step 809, a combination of spatial and temporal frequencies is selected that has a second marking but not a first marking. This combination is entered in storage device 19 for use during inspection at probe to top op borehole distances where the diameters and thicknesses of the two concentric steel pipes as provided in first step 801 have been used.

From a tenth step 810 the process repeats from first step for a different combination of the diameters and thicknesses of the two concentric steel pipes, until all combination of the diameters and thicknesses of the two concentric steel pipes that occur in the well bore have been processed.

The invention claimed is:

1. A method of monitoring cement defects in a well bore that comprises an inner metal pipe, the well bore having different well bore configurations outside the inner metal pipe at different distances from the top of the borehole, the method comprising using a probe that comprises a support structure that extends in an axial direction of the well bore, an ultrasound transmitter and a series of ultrasound receivers mounted at successive positions along the axial direction, wherein the method comprises
    moving the probe through the inner metal pipe along the axial direction of the well bore;
    transmitting an ultrasound signal from the transmitter into the inner metal pipe;
    receiving responses to the transmitted signal at the series of ultrasound receivers;
    band pass filtering the received responses to pass selectively a part of the response in a spatiotemporal frequency pass band corresponding to a predetermined apparent velocity component of wave travel along the axial direction at the ultrasound receivers and/or a predetermined combination of temporal and spatial frequency corresponding to the predetermined apparent velocity component.

2. A method according to claim 1, comprising pressing the transmitter against the inner surface of the inner metal pipe during said transmitting of the ultrasound signal from the transmitter.

3. A method according to claim 1, wherein the predetermined apparent velocity is determined by retrieving a predetermined apparent velocity setting dependent on a distance from the top of the borehole to the transmitter when the ultrasound signal was transmitted.

4. A method according to claim 3, comprising retrieving a plurality of selections of respective spatial frequencies, apparent velocities and/or a combination of temporal frequency and spatial frequency, dependent on said distance;
band pass filtering the received responses to pass selectively respective parts of the response in a pass band at the respective selected spatial frequencies, apparent velocities and/or combinations of temporal and spatial frequency.

5. A method according to claim 1, wherein said transmitted ultrasound signal is a pulse signal and said band pass filtering comprises computing a filtered time domain signal, the method comprising
detecting an earliest returned pulse in the filtered signal
determining time of arrival, amplitude and/or wave phase of the earliest pulse relative to the transmitted pulse and
comparing the time of arrival, amplitude and/or wave phase with a base line value.

6. A method according to claim 5, wherein the time of arrival, amplitude and/or phase determined at one or more other distances from the top of the borehole to the transmitter are used to provide the base line value.

7. A method according to claim 6, wherein the predetermined temporal frequency band comprises at least temporal frequencies between 15 kHz and 45 kHz and effectively no temporal frequencies above 50 kHz.

8. A method according to claim 5, comprising retrieving the predetermined apparent velocity of said waves, dependent on a distance from the top of the borehole to the transmitter, wherein said band pass filtered time domain signal corresponds to obtaining a sum of the received responses within a predetermined temporal frequency band, delayed relative to each other by time delays corresponding to the selected apparent velocity.

9. A method according to claim 1, comprising generating an inspection log indicating distances from the top of the borehole and/or ranges of distances from the top of the borehole where a difference between the time of arrival, amplitude and/or wave phase and a base line value exceeds a threshold value.

10. A well bore inspection system, comprising a support structure, an ultrasound transmitter on the support structure, a series of ultrasound receivers on the support structure at successively different axial distances from the ultrasound transmitter, and a processing system comprising an adaptable spatiotemporal frequency band pass filter configured to pass selectively a part of the response in a spatiotemporal frequency pass band corresponding to a selectable apparent velocity component of wave travel along the axial direction at the ultrasound receivers, and/or a combination of temporal and spatial frequency corresponding to the predetermined apparent velocity component.

11. A well bore inspection system according to claim 10, wherein the processing system being configured to determine a distance from the top of the borehole to the transmitter when the ultrasound signal was transmitted and to control the selectable apparent velocity of said waves and/or the combination of a temporal frequency and the spatial frequency dependent on an indication of a selection retrieved dependent on the distance from the top of the borehole.

12. A well bore inspection system according to claim 10, wherein the probe comprises a circular array of transmitters including said transmitter in a plane perpendicular to the axial direction of the well bore.

13. A well bore inspection system according to claim 12, wherein the probe comprises resilient elements configured to act between the supporting structure and a respective one of the ultrasound transmitters in the circular array, to push the ultrasound transmitter radially outward towards an inner surface of an innermost pipe of the well bore.

14. A well bore inspection system according to claim 10, wherein the probe comprises a plurality of columns of successive ultrasound receivers on the support structure at successively different axial distances from the ultrasound transmitters.

15. A well bore inspection system according to claim 10, wherein said band pass filtering comprises computing a filtered time domain signal, wherein said processing system is configured to cause the ultrasound transmitter to transmit the ultrasound signal as a pulse signal, to detect an earliest returned pulse in the filtered signal, determine time of arrival, amplitude and/or wave phase of the earliest pulse relative to the transmitted pulse and to compare the time of arrival, amplitude and/or wave phase with a base line value.

16. A non-transitory computer readable medium, comprising instructions for a programmable processing system that, when executed by the processing system will cause said processing system to
receive detected responses to a transmitted signal at a series of ultrasound receivers at successively different positions along an axial direction in a well bore;
determine a distance from the top of a borehole to a transmitter that caused the responses when the ultrasound signal was transmitted;
band pass filter the received responses to pass selectively a part of the response in a spatiotemporal frequency pass band corresponding to a predetermined apparent velocity component of wave travel along the axial direction at the ultrasound receivers and/or a predetermined combination of temporal and spatial frequency corresponding to the predetermined apparent velocity component.

* * * * *